United States Patent
Campbell et al.

(10) Patent No.: US 6,206,918 B1
(45) Date of Patent: Mar. 27, 2001

(54) HEART VALVE PROSTHESIS HAVING A PIVOT DESIGN FOR IMPROVING FLOW CHARACTERISTICS

(75) Inventors: Louis A. Campbell; Monti R. Gourley, both of Austin, TX (US)

(73) Assignee: Sulzer Carbomedics Inc., Austin, TX (US)

(*) Notice: Subject to any disclaimer, the term of this patent is extended or adjusted under 35 U.S.C. 154(b) by 0 days.

(21) Appl. No.: 09/310,801

(22) Filed: May 12, 1999

(51) Int. Cl.[7] .......................................... A61F 2/24
(52) U.S. Cl. ......................................... 623/2.32; 623/2.28
(58) Field of Search ................................ 623/2.28, 2.29, 623/2.3, 2.31, 2.32

(56) References Cited

U.S. PATENT DOCUMENTS

| | | | |
|---|---|---|---|
| Re. 30,507 | 2/1981 | Kaster | 3/1.5 |
| 3,974,854 | 8/1976 | Kurpanek | 137/512 |
| 4,276,658 | 7/1981 | Hanson et al. | 3/1.5 |
| 4,363,142 | 12/1982 | Meyer | 3/1.5 |
| 4,605,408 | 8/1986 | Carpentier | 623/2 |
| 4,657,545 | 4/1987 | Zibelin | 623/2 |
| 4,689,046 | 8/1987 | Bokros | 623/2 |
| 4,692,165 | 9/1987 | Bokros | 623/2 |
| 4,979,955 | 12/1990 | Smith | 623/2 |
| 5,135,538 | 8/1992 | Pawlak et al. | 623/2 |
| 5,147,390 | 9/1992 | Campbell | 623/2 |
| 5,192,313 | 3/1993 | Budd et al. | 623/2 |
| 5,545,216 | 8/1996 | Bokros et al. | 623/2 |
| 5,545,487 | 8/1996 | Ishijima et al. | 428/548 |
| 5,554,184 | 9/1996 | Machiraju | 623/2 |
| 5,641,324 | 6/1997 | Bokros et al. | 623/2 |
| 5,741,328 | 4/1998 | Reif | 623/2 |
| 5,814,100 | 9/1998 | Carpentier et al. | 623/2 |

FOREIGN PATENT DOCUMENTS 31 28 704A  2/1983  (DE).
WO97/30658  8/1997  (WO).

OTHER PUBLICATIONS

Filbioloa, R. S., et al., On The Hemolytic And Thrombogenic Potential Of Occluder Prosthetic Heart Valves From In–Vitro Measurements, Journal of Biomechanical Engineering, May 1981, vol. 103, pp. 83–89.

Giersiepen, M., et al., Estimation Of Shear Stress–Related Blood Damage In Heart Valve Prostheses—In Vitro Comparison Of 25 Aortic Valves, Wichtig Editore, 1990, pp. 300–306.

Rubinson, R. M., et al., Mechanical Destruction of Erythrocytes By Incompetent Aortic Valvular Prostheses, Am. Heart J., Feb. 1966, pp. 179–186.

Hanle, D. D., et al., In Vitro Flow Dynamics Of Four Prosthetic Aortic Valves: A Comparative Analysis, J. Biomechanics, vol. 22, No. 67, 1989, pp. 597–607.

Informational Brochure: Sulzer Carbomedics, The Inside Story on Safety.

Informational Brochure: Sulzer Carbomedics, Product Catalog.

Informational Brochure: CarboMedics, 16mm and 18mm Prosthetic Heart Valves.

Informational Brochure: Considerations for the Clinical Use of the CarboMedics "Top Hat" Supra–Annular Aortic Valve.

*Primary Examiner*—Michael Milano
(74) *Attorney, Agent, or Firm*—Timothy L. Scott; Philip S. Lyren

(57) ABSTRACT

A heart valve prosthesis having improved flow characteristics. A heart valve prosthesis includes a valve body and a pair of leaflet occluders. The valve body includes an interior surface that defines a central passage for blood flow. The pair of leaflet occluders are pivotably mounted in the passage via ears or tabs that are received in recesses formed in the interior surface that defines the central passage. The recesses are formed with sloped sidewalls to improve the blood flow therethrough. The recesses are also formed such that the leaflet occluder ears act against at least two surfaces that limit the motion of the leaflet occluder to provide a more stable movement that is less damaging to blood cells.

21 Claims, 5 Drawing Sheets

HEART VALVE PROSTHESIS HAVING A PIVOT DESIGN FOR IMPROVING FLOW CHARACTERISTICS

FIELD OF THE INVENTION

The present invention relates generally to heart valve prostheses and, in particular, to an improved pivot design for the pivotable leaflet occluders.

BACKGROUND OF THE INVENTION

A variety of heart valve prostheses have been developed for use in hearts, such as human or animal hearts. The typical heart value prosthesis generally includes a main body portion having an annular shape and a central passage for blood flow. One or more leaflet occluders are mounted to the annular body for pivotable movement within the central passage. Such heart valve assemblies operate hemodynamically in conjunction with the pumping action of the heart for effective replacement of a defective natural heart valve.

A common heart valve construction is the bi-leaflet design in which two leaflet occluders are pivotably mounted in the annular body in an opposed relationship. The leaflet occluders are mounted such that when the heart valve is closed, each leaflet occluder covers approximately half of the valve opening or passage. Typically, each leaflet occluder is generally semi-circular in shape and includes a rounded exterior which engages an inner surface of the main body that defines the central passage. Each leaflet occluder also includes a generally linear edge portion designed to move proximate the linear edge portion of the opposing leaflet occluder when the valve is closed. Each leaflet occluder is mounted for pivotable movement about an axis disposed generally parallel with the linear edge.

In operation, as blood pressure rises in response to heart contraction, the leaflet occluders are pivoted from a closed position to an open position. In the open position, blood flows past the leaflet occluders through the heart valve passage. When the heart contraction is complete, however, the blood tends to flow in the opposite direction in response to pressure in the aorta. This causes the leaflet occluders to close and thereby maintain a pressure in the arterial system. Effectively, this type of heart valve prosthesis operates in substantially the same manner as a natural human heart valve.

Conventional leaflet occluders include opposing tabs or ears that are received in corresponding recesses formed in the interior surface defining the flow passage. Each pair of opposed recesses constrain the leaflet occluder mounted therein, and the walls of the recesses serve as stops to limit the pivoting motion of the leaflet occluders at closed and open positions. Exemplary prior art designs are illustrated and described in such patents as Hanson et al., U.S. Pat. No. 4,276,658, Bokros, U.S. Pat. No. 4,689,046, and Campbell, U.S. Pat. No. 5,147,390. Such prior art valves have generally proved to be very reliable, and have a projected life expectancy exceeding that of the patient. However, it is desirable to continually increase or enhance the performance characteristics of heart valve prostheses.

For example, problems can develop because of the design of the recesses for receiving the leaflet occluder ears. In many applications, it is desirable to design recesses with a contour providing at least two stops that act against the leaflet ear to limit the pivotable motion of a given leaflet occluder. By separating the stops that act against the ear, the angle at which the leaflet occluders close and/or open can be better controlled. The Hanson et al. reference and the Bokros reference cited above utilize recesses having narrowed throat regions and expanded outlying regions to provide at least two stops separated by a given distance that act against the leaflet occluder ear to limit a given pivoting motion.

Though such designs provide two stopping surfaces, they are typically limited by wall surfaces that are generally perpendicular to the interior surface that defines the blood flow passage of the heart valve. Such perpendicular surfaces often exist throughout the throat region of the recess and limit the ability of the blood to freely flow through the recessed area. As a result, blood clotting can occur in the vicinity of the pivot recesses.

It would be advantageous to provide a heart valve prosthesis with uniquely designed leaflet occluder pivot recesses able to facilitate better blood flow characteristics while providing stable control of the opening and closing of the leaflet occluders.

SUMMARY OF THE INVENTION

The present invention features a heart valve prosthesis comprising a valve body and a pair of leaflet occluders. The valve body includes an interior surface that defines a central passage for blood flow therethrough. The leaflet occluders are proportioned to be pivotably mounted within the central passage. Each leaflet occluder includes a pair of mounting ears, and the valve body includes a plurality of recesses for receiving the pairs of mounting ears. Each recess is bounded by a base surface and a sidewall. The sidewall defines a narrowed throat region, an upstream expanded region on one side of the throat region, and a downstream expanded region on a generally opposite side of the throat region. The sidewall slopes outwardly from the base surface to form an angle with a central recess axis along the entire length of the sidewall. Thus, there are no surfaces generally perpendicular to the interior surface of the valve body.

According to another aspect of the present invention, a heart valve prosthesis is provided that includes a valve body having an interior surface defining a central passage for conducting blood flow. The heart valve prosthesis also includes at least one leaflet occluder pivotably mounted to the valve body by a pair of pivots. The interior surface that defines the central passage includes at least one pair of recesses to receive the pair of pivots. Each recess is bounded by a continuously sloped sidewall extending between the interior surface and a recess base. Each recess further includes a narrowed throat region disposed such that the continuously sloped sidewall forms at least one pivot stop on each opposing side of the narrowed throat region. The pivot stops cooperate to limit pivotal motion of the at least one leaflet occluder.

According to yet another aspect of the present invention, a method is provided for facilitating blood flow through a prosthetic heart valve. The prosthetic heart valve is of the type including a valve body having an interior surface defining a central passage through which blood flows and a leaflet occluder pivotably mounted in the central passage by a pair of pivot ears. The method includes creating a first recess and a second recess in the interior surface on generally opposite sides of the central passage to receive a pair of pivot ears of an individual leaflet occluder. The method further includes forming each of the first recess and the second recess with a pair of expanded regions separated by a narrower throat region. The method further includes defining the first recess by a first sidewall and the second recess by a second sidewall. Additionally, the sidewalls are oriented at an angle throughout the narrower throat region and the pair of expanded regions to prevent the formation of surfaces that would be generally perpendicular to the interior surface of the valve body.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
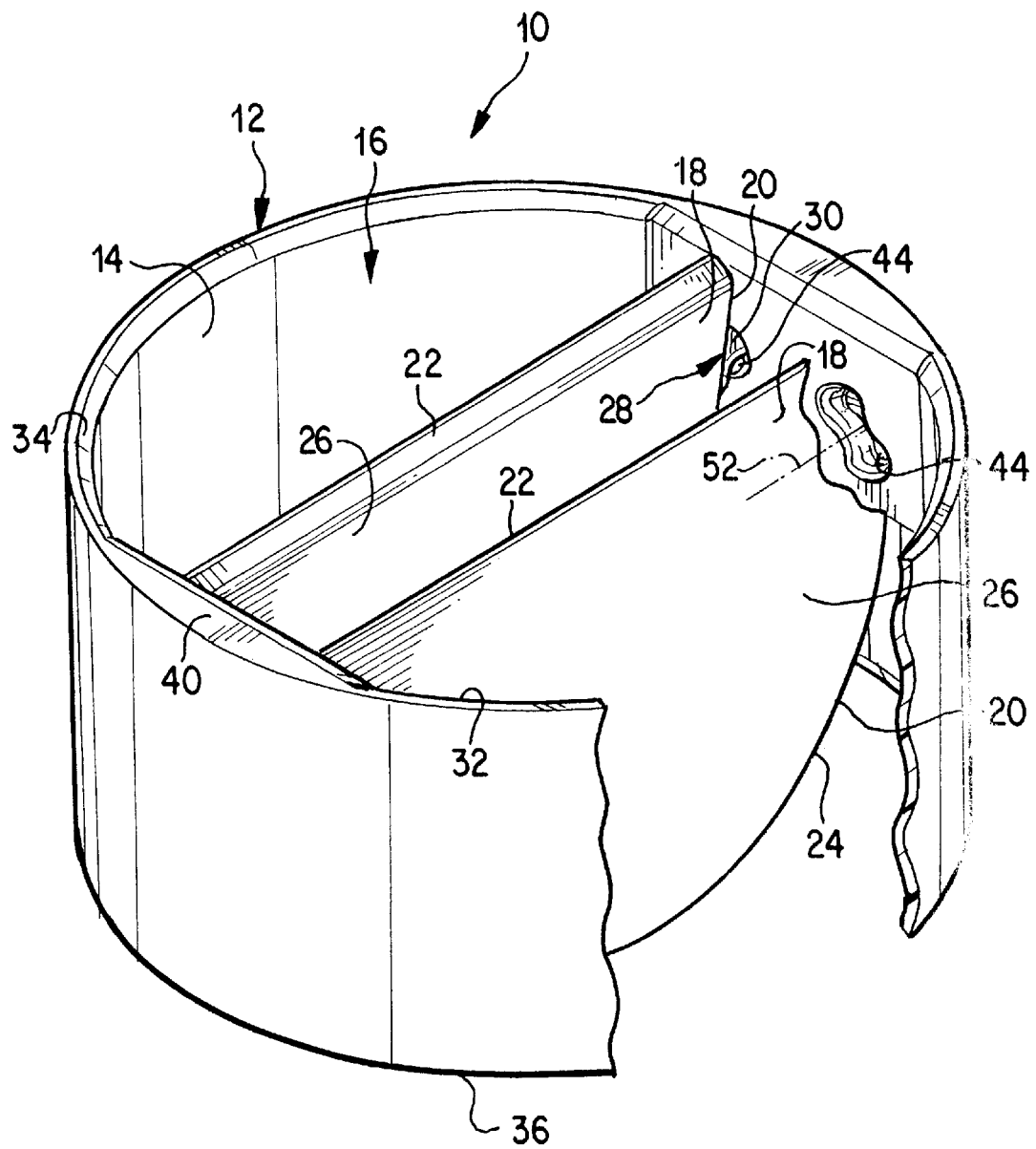
FIG. 1 is a perspective view of a heart valve prosthesis illustrating certain aspects of the present invention, and having one leaflet and a portion of the outer wall cut away to disclose a recess.

Referring generally to FIG. 1, a heart valve prosthesis 10 is illustrated according to one preferred embodiment of the present invention. Valve 10 includes a valve body 12 having a generally annular shape. Valve body 12 includes an interior surface 14 that defines a central passage 16 for conducting blood flow therethrough.

At least one leaflet occluder, and in this embodiment a pair of leaflet occluders 18, is pivotably mounted to valve body 12. In the illustrated embodiment, each leaflet occluder 18 includes a perimeter edge 20 having a generally linear lead edge 22 and a generally arcuate, semicircular, edge 24 designed to engage interior surface 14 of valve body 12 when valve 10 is in a closed position, as illustrated best in FIG. 2. Preferably, the leading edge 22 of each occluder 18 is formed at an angle that allows the two lead edges 22 to abut one another when valve 10 is in a closed position. (See FIG. 2). Similarly, arcuate edges 24 are formed at an angle to facilitate engagement with interior surface 14. (See FIG. 2). Each leaflet occluder 18 is further defined by a pair of generally flat opposing surfaces 26 that extend from lead edge 22 to arcuate edge 24.

Figure 2:
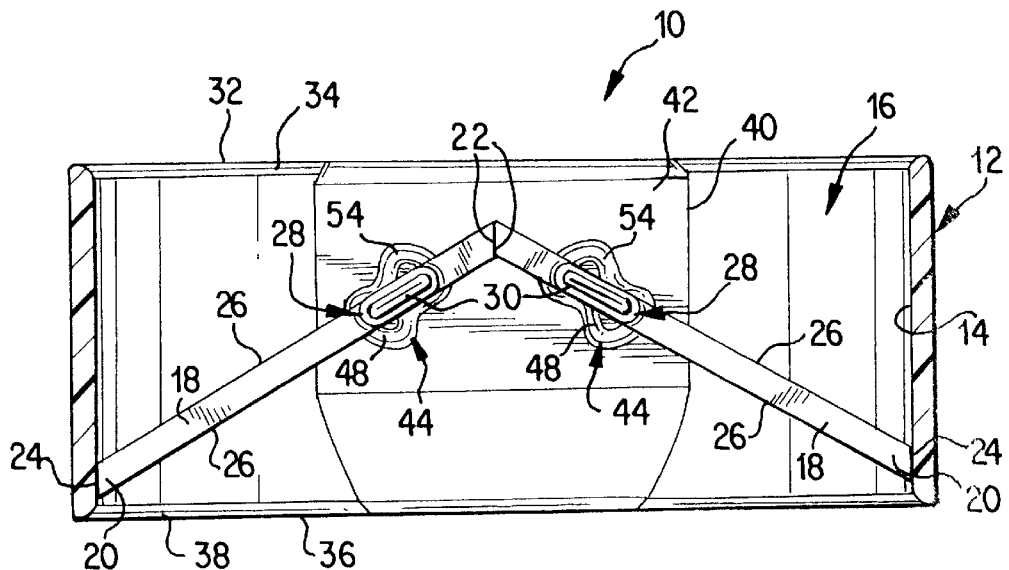
FIG. 2 is a cross-sectional view taken generally along the line 2—2 of FIG. 1, showing leaflets in a closed position.
Figure 3:
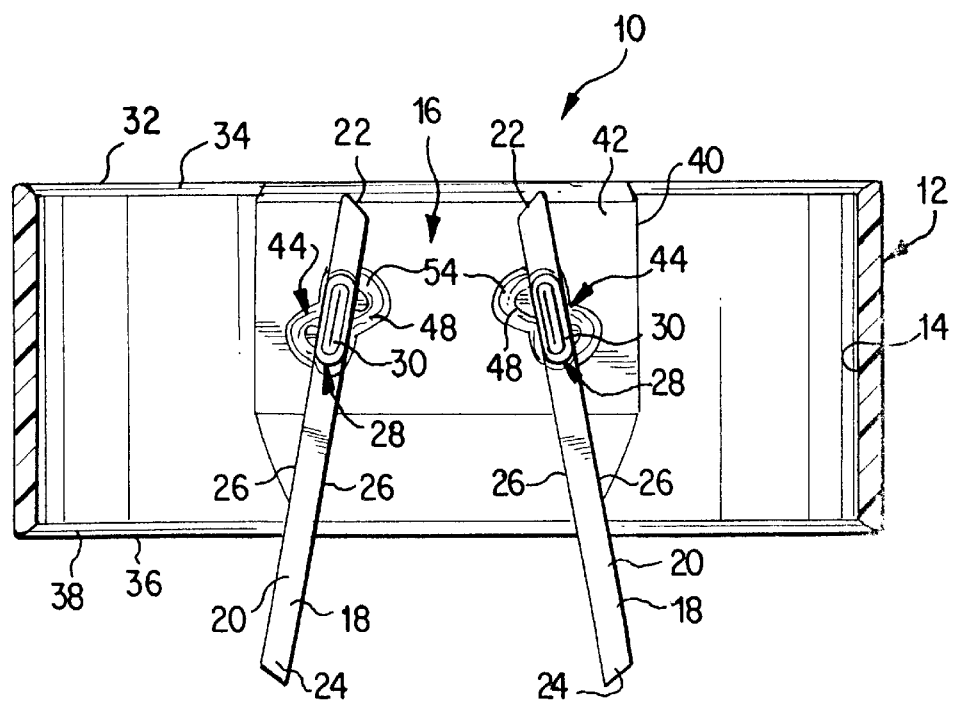
FIG. 3 is a cross-sectional view similar to that of FIG. 2 but showing the leaflets in an open position.

Each leaflet occluder 18 includes a pair of pivot structures 28 that permit the leaflets to pivot between the closed position illustrated in FIG. 2 and the open position illustrated in FIG. 3. In the particular embodiment illustrated, pivot structures 28 each include an ear 30 that is generally in the form of a flat tab extending outwardly from arcuate edge 24 a predetermined distance from lead edge 22, as illustrated in FIGS. 1 through 3.

The exemplary valve body 12 is designed to facilitate blood flow therethrough and to pivotably receive leaflet occluders 18. Specifically, valve body 12 includes an upstream edge 32 having a filleted region 34 and a downstream edge 36 having a filleted region 38. Filleted regions 34 and 38 help provide a smooth transition of blood through central passage 16.

Valve body 12 further includes a pair of thickened or reinforced regions 40 that are generally opposed to one another across central passage 16. Each reinforced region 40 is defined in part by an inward surface 42 that typically is generally flat. Inward surface 42 is part of overall interior surface 14 of valve body 12 but interrupts the otherwise generally cylindrical configuration of interior surface 14.

Reinforced regions 40 are designed to accommodate a plurality of recesses 44 for receiving leaflet occluder ears 30. In the illustrated embodiment, there are two pairs of opposed recesses 44, and each pair of opposed recesses is located to receive opposed ears 30 of one of the leaflet occluders 18. The contour and placement of recesses 44 is selected to limit the range of movement of leaflet occluders 18 between the closed position illustrated in FIG. 2 and the fully open position illustrated in FIG. 3. The unique design of recesses 44 provides for controlled movement of leaflet occluders 18 while enhancing the flow characteristics of blood flowing past recesses 44 as it moves through central passage 16.

Figure 4:
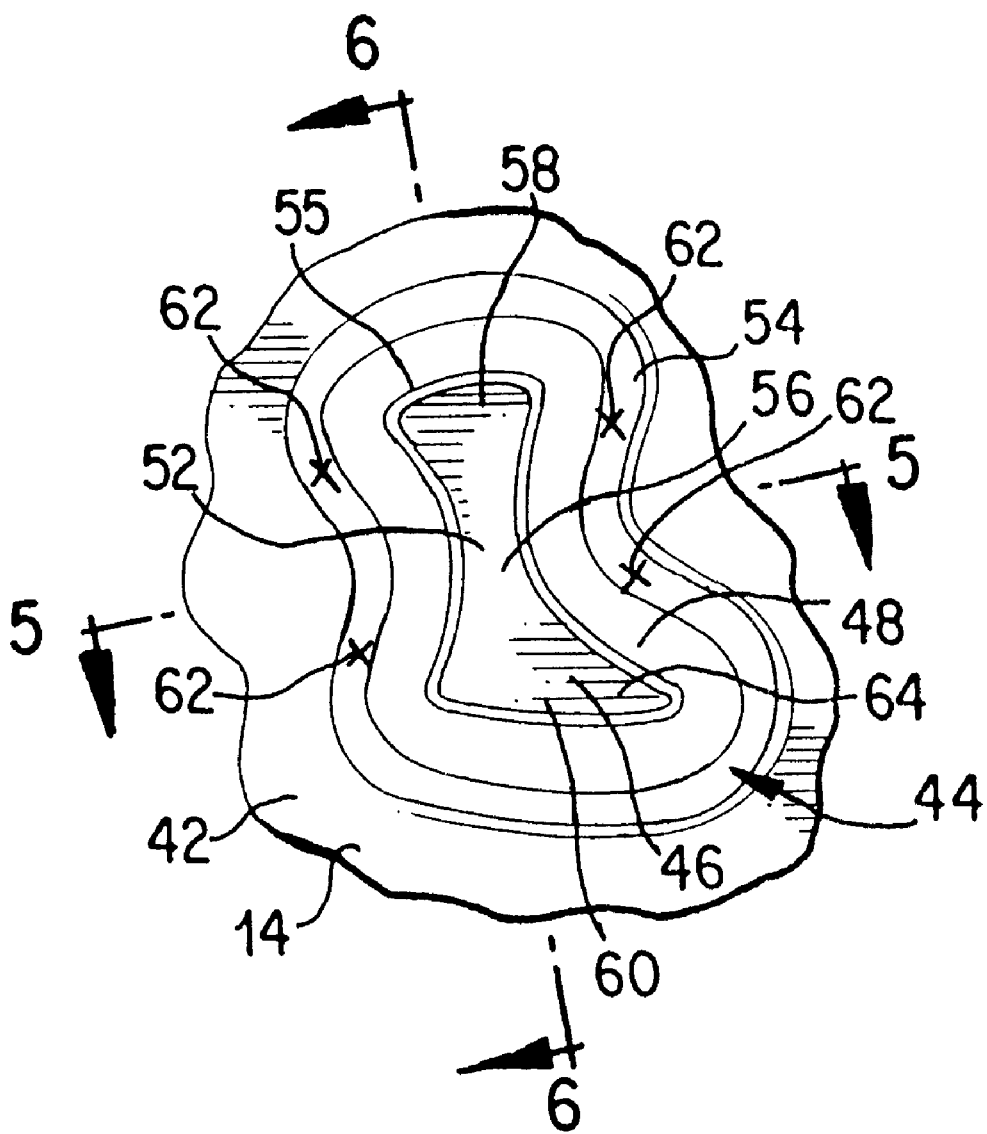
FIG. 4 is an expanded front view of a recess, according to an exemplary embodiment of the present invention.

Referring generally to FIG. 4, a preferred, exemplary embodiment of one of the recesses 44 is illustrated. The illustrated recess is oriented the same as the rightmost recess illustrated in FIG. 3. However, the leftmost recess illustrated in FIG. 3 is simply a mirror image of the rightmost recess, and the following description applies equally. In fact, the following description can be assumed to apply equally to each of the four recesses required for the embodiment illustrated in FIGS. 1–3.

Figure 5:
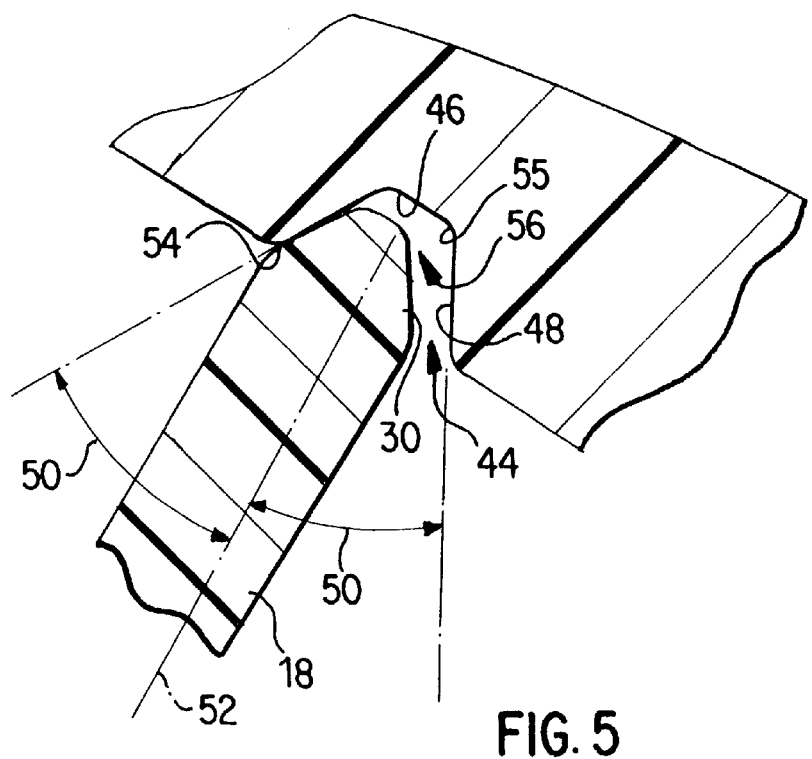
FIG. 5 is a cross-sectional view taken generally along line 5—5 of FIG. 4.
Figure 6:
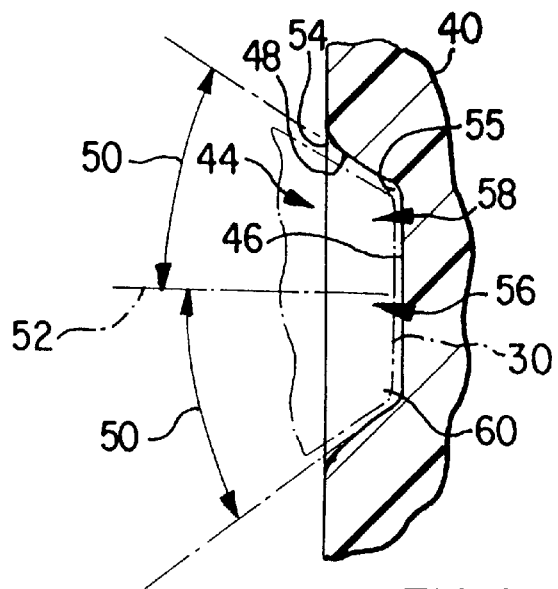
FIG. 6 is a cross-sectional view taken generally along line 6—6 of FIG. 4

Referring again to FIG. 4, recess 44 is bounded by a base surface 46 and a sidewall 48. Sidewall 48 is a sloped sidewall that extends between base surface 46 and interior surface 14. As illustrated, sidewall 48 slopes generally outwardly from base surface 46 to interior surface 14. In other words, sidewall 48 forms an angle 50 (see FIGS. 5 and 6) with a central axis 52 disposed through recess 44 generally normal to base surface 46 and interior surface 14. Angle 50 exists along the length of sidewall 48 to eliminate surfaces that are generally perpendicular with interior surface 14 i.e. generally parallel with central axis 52.

Potentially, angle 50 can vary in degree at different points or locations along sidewall 48, but typically it is substantially constant along the entire length of sidewall 48. In any event, angle 50 preferably is in the range from approximately 1° to approximately 45°; more preferably in the range from approximately 10° to approximately 35°; yet more preferably in the range from approximately 25° to approximately 35°; and most preferably approximately 30°.

Sidewall 48 preferably includes an outermost edge or fillet 54 that is arcuate in shape to further facilitate the transition of blood through recess 44. Preferably, the arcuate edge 54 also provides a rounded edge for contact with a given leaflet occluder ear 30 as the ear 30 pivots to the limit of its motion in recess 44. Having arcuate edge 54 at the point of contact reduces the Hertzian contact stresses which, in turn, reduces the amount of impact wear on the components relative to a sharp edge contact.

Between base surface 46 and outermost edge 54, sidewall 48 is illustrated as generally flat, but this should not be construed as limiting. Potentially, this sidewall can provide a slightly arcuate surface or other contour in the transition direction from interior surface 14 to base surface 46. Also, an arcuate transition or fillet 55 is disposed between sidewall 48 and base surface 46. Fillet 55 improves the fluid washing at the bottom of the recess 44.

Furthermore, sidewall 48 includes a lengthwise contour that enhances the stability of the leaflet occluder 18 when it moves to a fully open or fully closed position. Specifically, the lengthwise contour of sidewall 48 forms recess 44 with a narrowed throat region 56, an upstream expanded region 58, and a downstream expanded region 60. This configuration allows each recess 44 to be formed with multiple stops or stop areas 62. Sidewall 48 is configured such that stop areas 62 exist on opposite sides of central axis 52 and throat region 56. Preferably, a given leaflet occluder ear 30 contacts two stop areas whenever it reaches its limit of travel.

Figure 7:
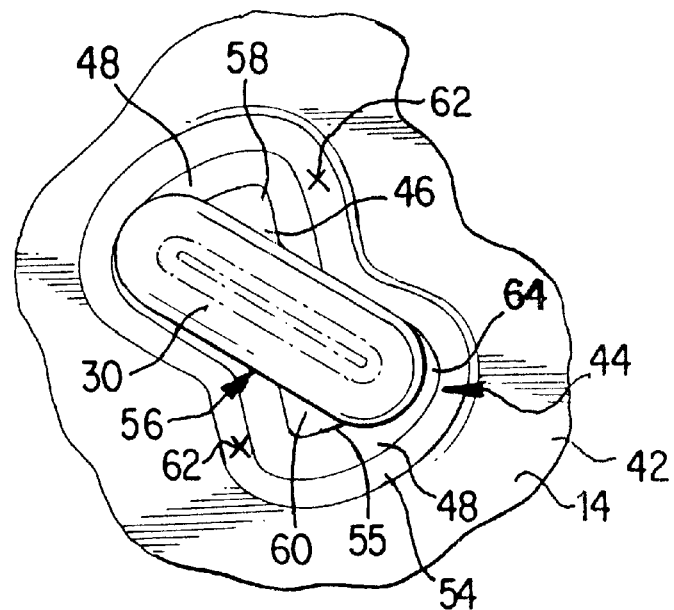
FIG. 7 is a front view similar to that of FIG. 4 but showing a leaflet ear in dashed lines in a closed position.
Figure 8:
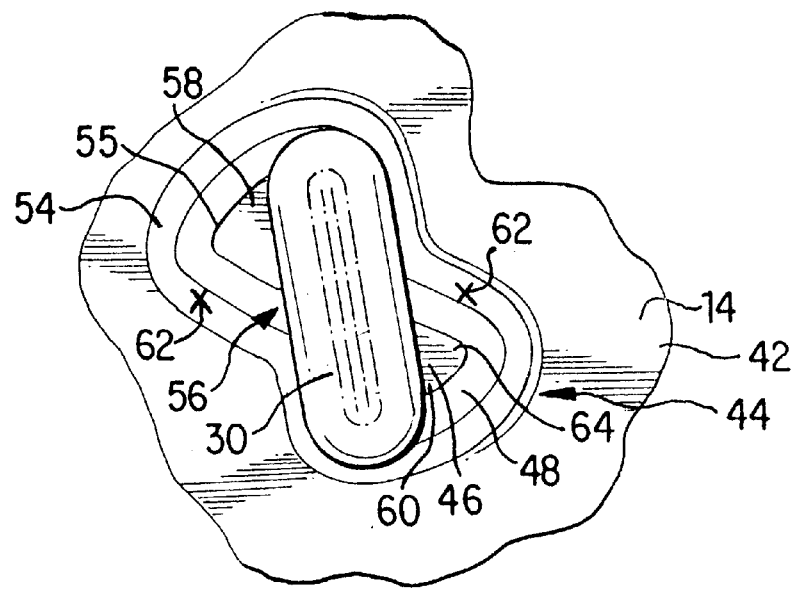
FIG. 8 is a front view similar to that of FIG. 4 but showing a leaflet ear in dashed lines in an open position.

For example, as illustrated in FIG. 7, leaflet occluder 18 and its attached ear 30 are in a closed position abutting two stop areas 62. Similarly, as illustrated in FIG. 8, ear 30 abuts sidewall 48 at two stop areas 62 when leaflet occluder 18 and ear 30 are in an open position. Downstream expanded region 60 may include an extended portion 64 that effectively increases the radius of curvature of sidewall 48 at the adjacent stop 62. In this particular design, the extended portion 64 increases the leaflet/orifice contact area so the contact stresses are reduced and it also avoids over constraining the leaflets in the fully closed position when the straight edges 22 of the two leaflets are in contact, and the accurate edges of the leaflets 24 are in contact with the inside surface 14 of the orifice.

The combination of the sloped sidewall 48 with its unique overall contour provides for greater control of the leaflet occluders 18 via multiple stop areas 62 while reducing the risk of blood clotting proximate recesses 44 by providing the sidewall with an appropriate slope. As described above, the actual slope angle of sidewall 48 can vary, but a desirable, exemplary angle is approximately 30° from a normal axis, because this angle provides relatively smooth transition of the blood flowing past a given recess 44 while remaining steep enough to provide a solid abutment surface for the corresponding ear 30 at each stop area 62.

It will be understood that the foregoing description is of preferred exemplary embodiments of this invention, and that the invention is not limited to the specific forms shown. For example, a variety of valve body configurations may be utilized; the number, shape and size of the leaflet occluders can be changed depending on the specific design; the materials utilized for the given components, e.g. pyrolytic carbon, are well known to those of ordinary skill in the art, but those materials can be changed according to specific applications or advances in material technology; and the contour of the leaflet occluder ears as well as the shape of the base and sidewall can be adjusted accordingly. These and other modifications may be made in the design and arrangement of the elements without departing from the scope of the invention as expressed in the appended claims.

What is claimed is:

1. A heart valve prosthesis, comprising:
    a valve body having an interior surface that defines a central passage for blood flow therethrough; and
    a pair of leaflet occluders proportioned to be pivotably mounted within the central passage, each leaflet occluder including a pair of mounting ears;
    wherein the valve body includes a plurality of recesses for receiving the pairs of mounting ears, each recess being bounded by a base surface and a sidewall, the sidewall defining a narrowed throat region, an upstream expanded region on one side of the throat region and a downstream expanded region on a generally opposite side of the throat region, the sidewall sloping outwardly from the base surface to form an oblique angle with a central axis along the entire length of the sidewall.

2. The heart valve as recited in claim 1, wherein the oblique angle remains constant along the entire length of the sidewall.

3. The heart valve as recited in claim 1, wherein the oblique angle is in the range from approximately one (1) degree to approximately forty five (45) degrees.

4. The heart valve as recited in claim 1, wherein the oblique angle is in the range from approximately ten (10) degrees to approximately thirty five (35) degrees.

5. The heart valve as recited in claim 1, wherein the oblique angle is in the range from approximately twenty five (25) degrees to approximately thirty five (35) degrees.

6. The heart valve as recited in claim 1, wherein the sidewall includes a plurality of stop regions disposed such that each mounting ear contacts at least two cooperating stop regions at an extreme of its pivotable motion.

7. The heart valve as recited in claim 6, wherein each stop region of the plurality of stop regions is disposed at a predetermined distance from a center of the throat region.

8. A heart valve prosthesis, comprising:
    a valve body having an interior surface that defines a central passage for conducting blood flow; and
    at least one leaflet occluder pivotably mounted to the valve body by a pair of pivots, the interior surface including at least one pair of recesses to receive the pair of pivots, each recess being bounded by a continuously obliquely sloped sidewall extending between the interior surface and a recess base, each recess further including a narrowed throat region disposed such that the continuously obliquely sloped sidewall forms at least one pivot stop on each opposing side of the narrowed throat region to facilitate limiting the pivotal motion of the at least one leaflet occluder.

9. The heart valve prosthesis as recited in claim 8, wherein the at least one leaflet occluder comprises a pair of leaflet occluders.

10. The heart valve prosthesis as recited in claim 8, wherein the at least one pair of recesses includes four recesses.

11. The heart valve prosthesis as recited in claim 10, wherein each pivot of the pair of pivots comprises a generally flat ear.

12. The heart valve prosthesis as recited in claim 8, wherein the continuously obliquely sloped sidewall slopes outwardly from the recess base to form an oblique angle with an axis disposed generally normal to the interior surface, the angle being at least ten (10) degrees.

13. The heart valve prosthesis as recited in claim 12, wherein the oblique angle is in the range from approximately ten (10) degrees to approximately forty five (45) degrees.

14. The heart valve prosthesis as recited in claim 12, wherein the oblique angle is in the range from approximately twenty five (25) degrees to approximately thirty five (35) degrees.

15. A method for facilitating blood flow through a prosthetic heart valve that includes a valve body having an interior surface defining a central passage through which blood flows and a leaflet occluder pivotably mounted in the central passage by a pair of pivot ears, comprising:
    creating a first recess and a second recess in the interior surface on generally opposite sides of the central passage to receive a pair of pivot ears of an individual leaflet occluder;
    forming each of the first recess and the second recess with a pair of expanded regions separated by a narrower throat region;
    defining the first recess by a first sidewall and the second recess by a second sidewall; and orienting the first and the second sidewalls continously at an oblique angle selected to prevent formation of surfaces generally perpendicular to the interior surface.

16. The method as recited in claim 15, further comprising forming a third recess and a fourth recess to receive an additional pair of pivot ears of a second leaflet occluder.

17. The method as recited in claim 15, further comprising limiting the motion of the individual leaflet occluder by forming stop surfaces along the first sidewall in each expanded region of the first recess; and orienting the stop surfaces to interfere with a pivot ear of each pair of pivot ears.

18. The method as recited in claim 17, further comprising limiting the motion of the individual leaflet occluder by forming stop surfaces along the second sidewall in each expanded region of the second recess; and orienting the stop surfaces to interfere with a pivot ear of each pair of pivot ears.

19. The method as recited in claim 17, wherein orienting includes selecting oblique an angle in the range from approximately one (1) degree to approximately forty five (45) degrees as measured between an axis generally normal to the interior surface and the first sidewall or the second sidewall.

20. The method as recited in claim 17, wherein orienting includes selecting an oblique angle in the range from approximately twenty five (25) degrees to approximately thirty five (35) degrees as measured between an axis generally normal to the interior surface and the first sidewall or the second sidewall.

21. The method as recited in claim 15, further comprising placing a first fillet between the first sidewall and a first base surface of the first recess to improve fluid washing characteristics; and placing a second fillet between the second sidewall and a second base surface of the second recess to improve fluid washing characteristics.

* * * * *